(12) United States Patent
Solomon et al.

(10) Patent No.: US 9,393,004 B2
(45) Date of Patent: Jul. 19, 2016

(54) TISSUE PROTECTION SYSTEM AND METHOD

(71) Applicants: Theodore C. Solomon, Hempstead, MD (US); Clifford T. Solomon, Hempstead, MD (US)

(72) Inventors: Clifford T. Solomon, Hempstead, MD (US); Theodore C. Solomon, Hempstead, MD (US)

(*) Notice: Subject to any disclaimer, the term of this patent is extended or adjusted under 35 U.S.C. 154(b) by 201 days.

(21) Appl. No.: 14/068,982

(22) Filed: Oct. 31, 2013

(65) Prior Publication Data

US 2014/0309498 A1 Oct. 16, 2014

Related U.S. Application Data

(63) Continuation-in-part of application No. 13/863,290, filed on Apr. 15, 2013.

(51) Int. Cl.
| | |
|---|---|
| *A61B 17/02* | (2006.01) |
| *A61L 15/24* | (2006.01) |
| *A61L 15/26* | (2006.01) |
| *A61L 15/42* | (2006.01) |
| *A61F 13/00* | (2006.01) |
| *A61B 17/00* | (2006.01) |

(52) U.S. Cl.
CPC ........... *A61B 17/02* (2013.01); *A61F 13/00063* (2013.01); *A61F 13/00068* (2013.01); *A61L 15/24* (2013.01); *A61L 15/26* (2013.01); *A61L 15/425* (2013.01); *A61B 2017/00022* (2013.01); *A61B 2017/00889* (2013.01); *A61B 2017/00893* (2013.01); *A61B 2017/0212* (2013.01); *A61B 2217/005* (2013.01)

(58) Field of Classification Search
CPC ....................................................... A61L 15/16
See application file for complete search history.

(56) References Cited

U.S. PATENT DOCUMENTS

| | | | |
|---|---|---|---|
| 4,408,692 A | 10/1983 | Sigel et al. | |
| 5,679,423 A | 10/1997 | Shah | |
| 6,333,093 B1 | 12/2001 | Burrell et al. | |
| 7,005,556 B1 | 2/2006 | Becker et al. | |
| 2004/0133141 A1 | 7/2004 | Kiel et al. | |
| 2008/0006279 A1 | 1/2008 | Bodenham et al. | |
| 2008/0312572 A1 | 12/2008 | Riesinger | |
| 2011/0197897 A1 | 8/2011 | Touati | |
| 2012/0016325 A1* | 1/2012 | Pinto | A61F 13/00029 604/319 |
| 2012/0215193 A1* | 8/2012 | Siniaguine | A61F 13/0206 604/368 |
| 2012/0247487 A1 | 10/2012 | Llinas et al. | |

FOREIGN PATENT DOCUMENTS

| | | |
|---|---|---|
| WO | WO 2005/056059 | 6/2005 |
| WO | 2012054464 A2 | 4/2012 |

* cited by examiner

*Primary Examiner* — Andrew Yang
(74) *Attorney, Agent, or Firm* — Seed IP Law Group PLLC

(57) ABSTRACT

A protective tissue cover having a sleeve configuration to slide onto the working portion of a surgical instrument, such as a retractor. At least the contact side of the protective tissue cover is constructed from smooth antimicrobial material that minimizes contact irritation with tissue. Alternative embodiments include various multiple-ply constructions that incorporate an antimicrobial layer, an absorbent layer, and other medical layers to assist in surgical procedures.

9 Claims, 4 Drawing Sheets

TISSUE PROTECTION SYSTEM AND METHOD

CROSS REFERENCE TO RELATED APPLICATIONS

This application is a continuation-in-part of U.S. application Ser. No. 13/863,290, filed Apr. 15, 2013, entitled: Tissue Protection/Retraction System, the entire disclosure of which is expressly incorporated herein by reference.

BACKGROUND OF THE DISCLOSURE

This disclosure relates to medical devices, and particularly to a system and method for providing tissue protection that provides gentle, sterile, and non-aggravating contact with tissue.

In many respects, surgical (and some medical) procedures are very delicate processes. Much care and attention must be maintained not just with the procedure itself but also with the environmental conditions. Any invasive procedure runs the risk of potential contamination, infection, and inflammation as well as the occasional unforeseen complication to the patient. In modern medicine, many guidelines have been developed to minimize such dangers, such as protective apparel, specialized bandages and other surgical equipment, meticulous monitoring of tools and equipment used during surgery, and scrubbing or cleansing procedures for the surgeon, support staff, instruments and the surgical area.

One aspect of surgery that is of much concern is the handling of tissue during surgical and other medical procedures. Most conventional surgical procedures utilize surgical drapes around the incision site, providing a sterile barrier to prevent or reduce contamination. Special shapes of cotton/telfa, called paddies or cottonoids are used during surgery to facilitate dissection of normal tissue from abnormal such as a tumor removal or in order to remove the offending process or to lessen its size. In addition, we use similar techniques to dissect deeper into a normal area bringing us to an area of interest or pathology. Other examples may include objects placed on the surface of underlying tissue for protection. There are also processes in place for draping. Sometimes sponge-like materials are used for wicking fluids. These implements, while sterile, can cause trauma and irritation to the underlying tissue in and around the incision site, especially while dissecting delicate tissue during various surgeries including brain surgery. In some instances, there have been cases of cotton residue left in the surgical site, which is a potential hazardous complication for patient recovery. The residue can result in focal inflammation and/or infection. This may result in reoperation with possible significant morbidity and even mortality.

Besides the above implements, surgeons routinely use specialized tools, such as retractors, during the surgical procedure as a means of gaining access to critical anatomical sites and to keep surrounding tissue away from the target area. Retractor designs range from simple to complex, and retractors are typically constructed from surgical grade materials. Any contact of the retractors against exposed tissue, usually prolonged in most procedures where surrounding tissue must be isolated, can abrade or irritate the underlying tissue, causing potential inflammation leading to contamination and/or infection. Due to the complex biology of individuals, some patients and some tissues are more sensitive and susceptible to these types of complications.

In light of the above, it would be a benefit in the art of medicine to provide some means of minimizing these types of complications. Thus, a protective tissue cover solving the aforementioned problems is desired for internal and external use.

SUMMARY

Briefly, and in general terms, the system and method for providing tissue protection includes a non-stick and/or low friction membrane that enables a medical tool, device or dressing to contact body tissue without adhering to or damaging the tissue. In one embodiment, the system includes a protective tissue cover that includes a sleeve configuration having an outer contact surface with a closed end and an open end. The sleeve configuration slides onto the working portion of a surgical retractor or any other medical tool or device. At least the contact side of the protective tissue cover is constructed from smooth antimicrobial material that minimizes contact irritation with tissue and obviates residue during a surgical procedure. The contact side of the protective tissue cover may include a non-stick and/or low friction material. Alternative embodiments include various multiple-ply constructions that incorporate an antimicrobial layer, an absorbent layer, and other medical layers to assist in surgical procedures. Of course, it will be appreciated, that not every embodiment requires the anti-microbial material.

In another embodiment, the system and method includes a protective tissue cover having a membrane attached to the medical device to minimize or eliminate tissue contact friction and/or adhesion, and includes another layer of material for transporting substances directly to the contacted tissue. This added material can include medicaments such as heparin, thrombin, steroids, antibiotics, collagen, anti-epileptic medicaments, colorizing agents, immunoassay interrogators, anti-platelets and the like. Similarly, analgesics such as Lidocain, Marcane, and Novocain may be used internally or externally with the system and method described herein. Likewise, the protective tissue cover may include other substances for wicking away or absorbing fluids may be used.

In still another embodiment, the system and method includes attachable tools or devices that can be used, for example, to perfuse, irrigate and or suction areas of or adjacent to the contacted tissue. In other embodiments, the tools may be permanently attached to the protective tissue cover used herein.

Another embodiment of the system and method may include testing or diagnostic materials such as biomarkers, assays, testing strips, color indicators, and the like to determine the state of the contacted or adjacent tissue. It may even incorporate sensors to detect various conditions of the contacted and adjacent tissue.

In another embodiment, various substances used with the medical components need not include a protective sleeve or the like. In these embodiments, the antimicrobial material, medicaments, and/or analgesics can be placed directly upon the medical component via spraying, aerosolizing, dipping, painting or simply placing the material directly into, onto, and around the working space and any other applicable mechanism.

Another embodiment of the system and method can include using the non-stick, anti-adhesive material in association with a dressing and/or bandage so as to provide a frictionless and/or non-adhesive portion to attach to wounds, injured tissue and the like. The dressing or bandage of this embodiment may include antimicrobial material. This embodiment can likewise be used with any medicament, tool or other feature as discussed above. One use is with a burn patient.

It will be appreciated that any embodiment can be used with any type of medical or surgical device, medicament, attachable tool, dressing and the like. As such, this disclosure is not intended to be so limited.

These and other features will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
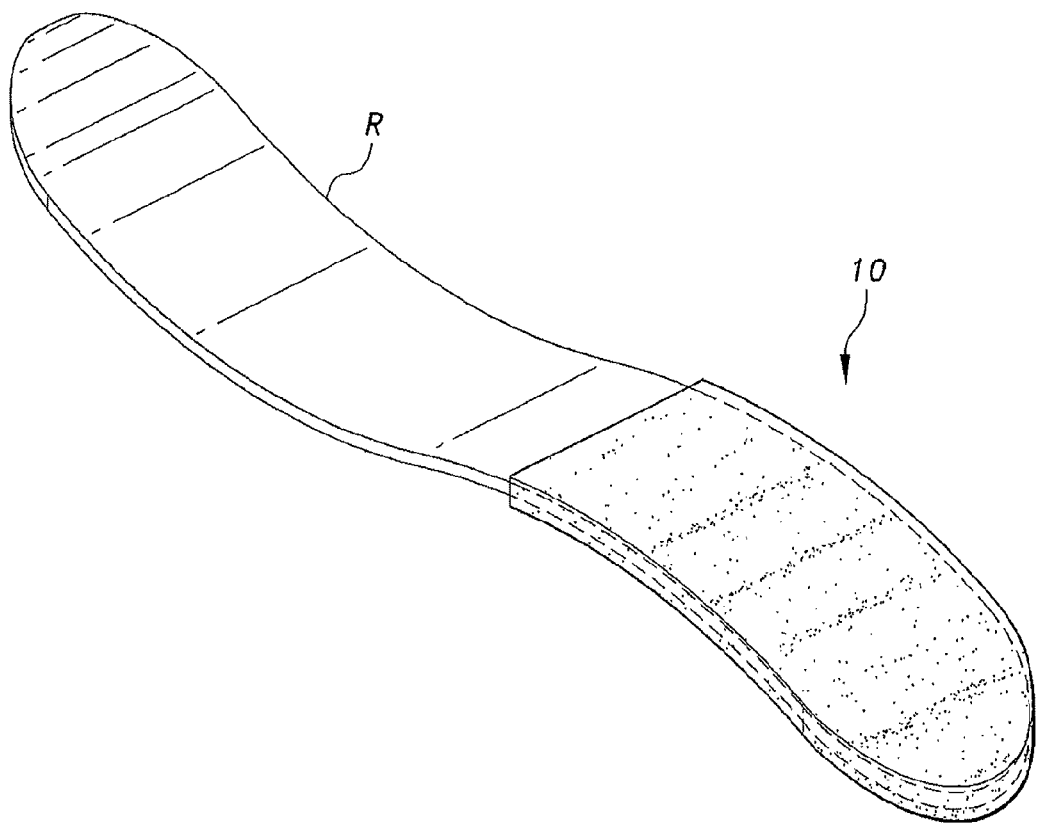
FIG. 1 is an environmental, perspective view of one embodiment of a protective tissue cover.

The protective tissue cover, a first embodiment of which is generally referred to by the reference number 10, provides a gentle, minimal irritant, sterile and/or antimicrobial, bactericidal layer between exposed tissue and environmental intrusions. As best seen in FIG. 1, the protective tissue cover 10 is constructed as a sleeve having a closed end and an opened end. The sleeve is configured to slide onto the working portion of a retractor R. In the drawing, the protective tissue cover 10 is shown attached to a curved ribbon retractor, but it is to be understood that the protective tissue cover 10 can be constructed to fit a variety of configurations of retractors, other medical instruments and the like. As an alternative, the protective tissue cover 10 can be used alone to function as a retractor.

The protective tissue cover 10 is preferably made from a smooth, resilient, polymeric material (medical grade) having sterile, antimicrobial and/or antiallergenic properties. The smoothness offers near frictionless contact with tissue through the interaction of natural biological fluids and/or solutions used in surgery between the material and tissue. This minimizes much of the potential abrading and irritation therewith, especially with tissue contact during surgery and the process of removing the retractor. It is to be understood that the benefits herein apply to any tissue that may be in contact with the protective tissue cover 10. Obviously, a sterile environment during surgery must be maintained at all times, and antimicrobial properties assure that this can be accomplished with minimal risk to the patient. As mentioned previously, some patients may exhibit hypersensitivity to certain materials or chemicals, and antiallergenic properties insure that the protective tissue cover 10 can be utilized for as wide a spectrum of patients as possible.

One example of an antimicrobial and antiallergenic material is Ioban®, manufactured by 3M, which is primarily a surgical drape impregnated with iodine. This particular material has been shown to be an effective antimicrobial barrier during surgical procedures. Other types of materials include, but are not limited thereto, medical grade elastomeric material, such as Silastic®, manufactured by Dow Corning, and other silicone elastomers and the like, that are impregnated or synthesized with chlorhexadine, collagen, vitamin D, quaternary amines, halamine, silver, combinations and the like. It is to be understood that some of these chemicals or compounds may exhibit toxicity at high levels of concentration. Thus, the composition must be made with due consideration for minimizing risks of toxicity. Another example includes materials such as Telfa®, a dressing produced by Kendall Company, and the like. Telfa® exhibits anti-adhering properties while providing absorption of fluids. Of course, it will be appreciated that other substances, antimicrobial or not, may be used herein.

Figure 2:
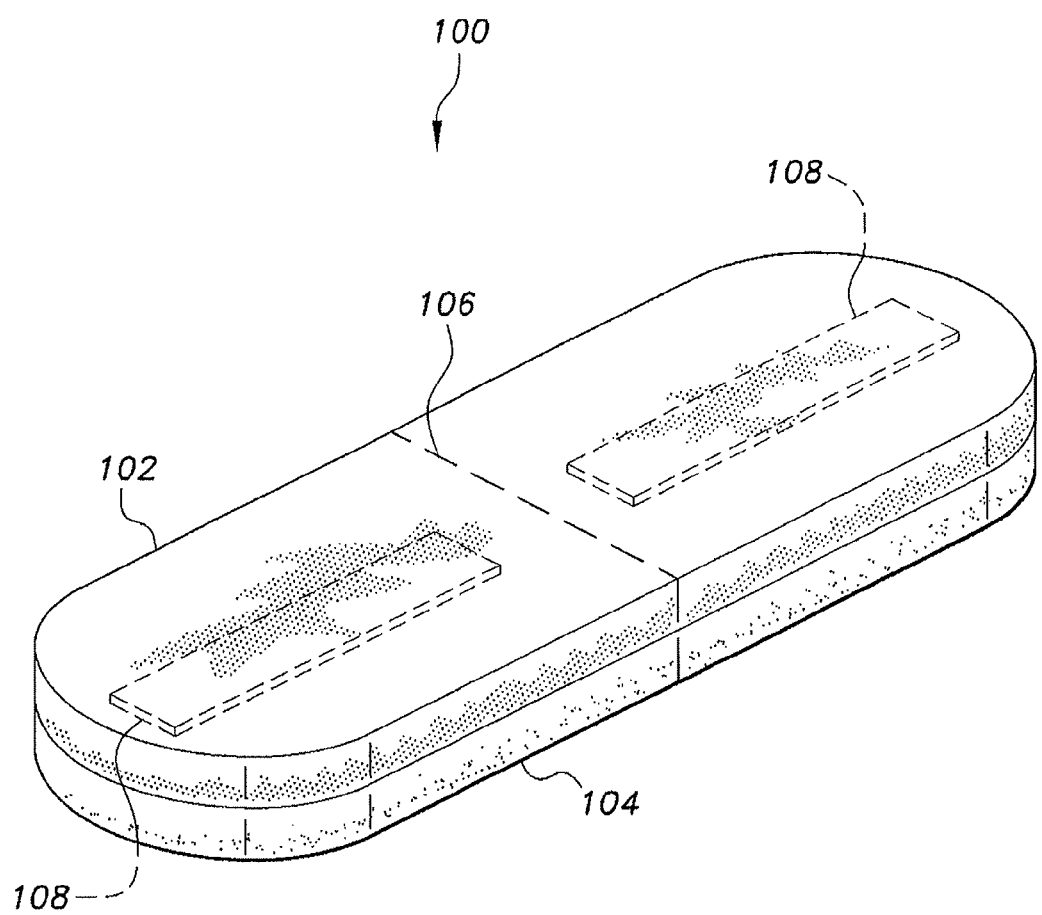
FIG. 2 is a perspective view of an alternative protective tissue cover in the form of discrete sheets.

An alternative protective tissue cover 100 is shown in FIG. 2. In this embodiment, the protective tissue cover 100 is constructed in the form of multiple webs or sheets for use as a protective layer for the underlying tissue. As shown, the protective tissue cover 100 has multiple layers of material, including a first or upper layer 102 and a second or lower layer 104. The upper layer 102 may be constructed from the same sterile and/or antimicrobial material mentioned above, while the lower layer 104 is preferably constructed from absorbent material, such as cottonoid® (cottonoid is a trademark of Johnson & Johnson of New Jersey; although the trademark was originally applied to a felted absorbent cotton, more recently the trademark has been applied to synthetic material, such as rayon, that absorbs moisture) and the like. In most uses, the upper layer 102 is preferably the layer in contact with tissue, while the lower layer 104 provides wicking of biological fluids, such as blood, mucous, and other fluids encountered during the course of the surgical procedure. Some or all portions of the upper layer 102 can also be provided with a biological adhesive layer for securing the protective tissue cover 100 as needed. To prevent undue abrasion, the adhesive portions should be applied to areas where irritation from abrasion is minimal or non-existent. The flexibility of the upper layer 102 eases application of the protective tissue cover 100 onto tissue by easily conforming to the contours thereof. In addition, the protective tissue cover 100 can be provided with at least one perforation 106 so that the user can tear off smaller sections of the protective tissue cover 100, as desired.

The lower layer 104 or the absorbent layer may be constructed from material that is resistant to leaving residue. For example, many barriers exist that are constructed from cotton products. However, they tend to adhere to tissue or left in-situ unintentionally. This type of situation often results in unintended trauma to the tissue due to a peeling effect on the tissue when attempting to remove the same. Thus, while cotton products exhibit great absorption, they and similar products should be constructed to minimize adherence characteristics.

In this embodiment, the upper layer 102 can also be provided with at least one detection strip 108 embedded in the upper layer 102. As previously mentioned, the use and number of surgical equipment is closely monitored during surgery. There have been cases where cottonoid paddies or other implements have been accidentally overlooked and left in the body of the patient. This requires an immediate response and removal of the foreign matter before complications can occur. In order to avoid and minimize the dangers of such occurrences, especially from human error, the detection strip 108 permits early detection, via intra-operative or post-operative X-ray, CAT or MRI scan, of such potentially overlooked foreign matter. The composition of the detection strip 108 can include barium and salts, and compounds thereof, non-ferromagnetic metals, plastic, detectable coatings, or any other material that can provide discernible contrast in X-ray scans or molecular excitations. Other detection methods and materials can include coatings detectable via various bands of light. In other embodiments, the detection strip can be disposed in the lower layer 104 or in between the upper layer 102 and the lower layer 104.

Figure 3:
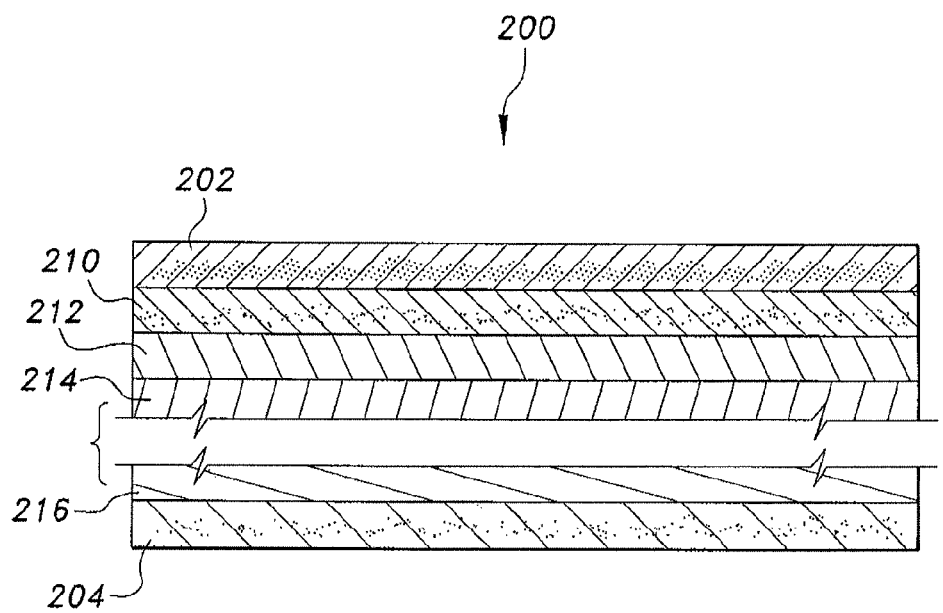
FIG. 3 is a sectional view of another alternative protective tissue cover.

A still further alternative protective tissue cover 200 is shown in FIG. 3. In this exemplary embodiment, the protective tissue cover 200 is constructed from a plurality of plies of material 202, 204, 210, 212, 214, 216. As shown, the protective tissue cover 200 includes a first or upper layer 202 constructed from the same sterile and/or antimicrobial material mentioned above while the second or lower layer 204 is preferably constructed from absorbent material such as cottonoid and the like. The intermediate layers 210, 212, 214, 216 each can be composed of various materials tailored to the requirements of the user. For example, one of the intermediate layers can be a detection layer similar to the detection layer 108 mentioned above, another can be composed of controllable thermogenic materials that can retain cold or heat for a given or user-defined duration, and still another can be a medicinal material including medicament, with or without time-release properties. The multiple layered construction of the protective tissue cover 200 allows for a variety of ply configurations tailored for the needs of the surgical procedure and/or patient requirements.

Figure 4:
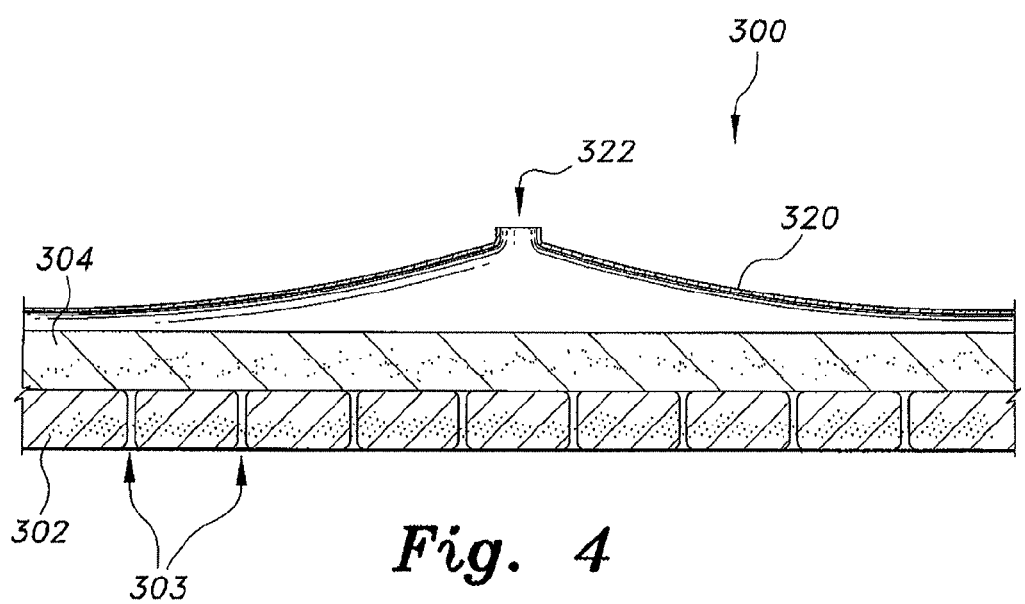
FIG. 4 is a sectional view of yet another alternative protective tissue cover with features for positive suctioning of fluids.

A further alternative protective tissue cover 300 is shown in FIG. 4. In this embodiment, the protective tissue cover 300 includes features for easy removal of fluids during surgical procedures. As shown, the protective tissue cover 300 includes a first layer 302 and a second layer 304. The first layer 302 is constructed from the same sterile and/or antimicrobial material mentioned above, while the second 304 is preferably constructed from absorbent material, such as cottonoid® and the like. Unlike the previous embodiments, the first layer 302 includes a plurality of microtubes 303 that permit flow of fluids between the layers. These microtubes 303 can be formed in various processes such as molding, laser or mechanical perforations, or chemically induced formations.

The protective tissue cover 300 can be provided with an outer shroud or cap 320 that surrounds select portions or all of the layers 302, 304. An adapter opening or nipple 322 is formed on the outer shroud 320 for selective attachment of a remote suction device (not shown). This configuration permits positive suctioning and/or irrigation of excess fluids through the protective tissue cover 300 during the surgical procedure. As an alternative, the outer shroud 320 can be removed and suctioning can be performed on the exposed surfaces of the layers 302, 304.

It will be appreciated that the embodiments described above and hereafter are not limited to use with retractors, but may also be used with any other type of medical tool, device, dressing or the like (components).

In one embodiment, the medical device does not include a sleeve. In this embodiment, the non-adhesive, low friction substance, which may include an antimicrobial substance and/or medicament, is applied directly to the medical tool, device and/or dressing. By way of example only, such application techniques may include spraying the substances onto the device or dressing, dipping the component into a non-adhesive substance, painting, aerosolizing, or any other mechanism for so applying to the component. Such substances can include Teflon, polymeric materials and the like. Any suitable substance may be used.

In addition, it will be appreciated that supplemental substances can be used with any of these embodiments, including but not limited to medicaments (such as heparin, thrombin, antibiotics, steroids, anti-inflammatories, collagen, anti-platelets, temperature control substances, and the like). Similarly, analgesics may be used such as, but not limited to Lidocain, Marcane, and Novocain. Substances for wicking away moisture and other fluids may likewise be used herein. Still further, microtubes or the like (as discussed above) can be used to remove fluid from the tissue and adjacent areas.

In another embodiment, tools or devices may be attached (temporarily or permanently) to the components. For example, perfusion devices, irrigation devices and suction devices can be employed. In one embodiment, irrigation may be used by attaching to the medical component a "Y" connector or additional port to enable fluids to be expelled from the device. By opening and closing the port, various amounts of fluid may be dispensed. In this way, such fluid can reduce the adhesion and/or friction of the device against or adjacent to the tissue. This might be particularly helpful when the retraction is removed. This feature can be used on any medical component, including, but not limited to Cobb suckers, suture needles, suture material, wound vacuums, dissectors, retractors and the like.

It will also be appreciated that the various other substances used with the medical components need not include a protective sleeve, membrane or the like. In these embodiments, the substances can be placed directly upon the medical component via spraying, aerosolizing, dipping, painting or any other applicable mechanism. For example, using such a device with a wound vacuum will prevent tissue adhesion from occurring as the vacuum or other components are removed from a wound. Similarly, with burn related injuries, analgesics, antibiotics and other medicaments can be applied while simultaneously preventing tissue adhesion during removal or dressings from the wound. This minimizes infection, reduces healing time and significantly reduces or eliminates pain for the patient.

In other embodiments, diagnostic and/or testing materials may be used with the system and method. For example, biomarkers, test strips, assays and the like may be used. In this way, the state of the tissue may be readily determined. For example, using these devices, the tissue can be determined to be free of infection, cancer, PH levels and the like during medical treatment. In some embodiments, such diagnostic and testing substances can be used to react to the tissue condition and to change color to indicate the presence or absence of various substances, e.g., infection, cancer, PH levels, medicaments, and the like.

Figure 5:
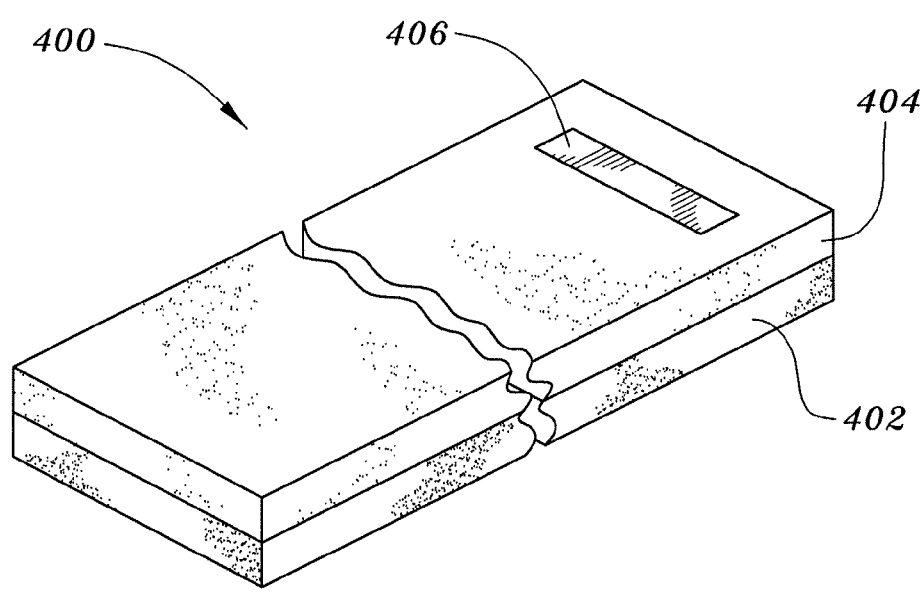
FIG. 5 is a perspective view of an alternative protective tissue cover in the form of a dressing or bandage.

In another embodiment shown in FIG. 5, a medical dressing or bandage 400 uses the non-adhesive and/or low friction features described herein. In this way, the dressing 400 can be applied and removed without causing injury to the tissue. Similarly, the dressing may include the various substances and/or tool and devices discussed above to aid in the medical treatment and healing of the contacting and adjacent tissue. For instance, the bandage 400 may include an upper layer 404 and a lower layer 404, similar to layers 102 and 104 shown and described with reference to FIG. 2. In certain embodiments, the dressing 400 includes the non-adhesive and/or low friction coefficient with the various substances in the middle, as shown and described with reference to FIG. 3. In another embodiment, the dressing 400 includes a similar cross-section shown in FIG. 4, with or without the outer shroud 320. The outer perimeter or edges of the dressing can include appropriate attachment means 406, such as clips, Velcro, male/female seals, adhesive and the like to enable the proper substances to contact the tissue without causing injury during use or upon removal. Further, the outer surface, or the surface not in contact with tissue, of the dressing 400 may include a protective coating, such as a polymer or other substance, to protect the dressing. Typically the upper layer 404 will be in contact with the tissue, however, the lower layer 404 may be in contact with the tissue.

Similarly, it will be appreciated that the embodiments may be used either internal or external to a patient. Any combination of device, component, substance and application may be used without departing from the disclosure herein.

It is to be understood that the embodiments are not limited to the embodiments described above, but encompasses any and all embodiments within the scope of the disclosure.

We claim:

1. A protective tissue cover, comprising:
    a first layer having a smooth surface and including an antimicrobial material;
    a second layer having the same shape as the first layer and connected to the first layer, and the second layer including an absorbent material; and
    a third layer disposed between the first layer and the second layer, the third layer includes medicaments, which are transported directly to tissue in contact with the protective tissue cover during a surgery.

2. The protective tissue cover of claim 1, wherein the first layer includes a polymer impregnated with at least one antimicrobial selected from the group consisting of iodine, chlorhexadine, collagen, vitamin D, quaternary amines, halamine, and silver.

3. The protective tissue cover of claim 2, wherein the second layer includes at least one material selected from the group consisting of polymers and residue-resistant cotton.

4. The protective tissue cover of claim 1, further comprising a detection strip embedded in the first layer.

5. The protective tissue cover of claim 4, wherein the detection strip comprises at least one material selected from the group consisting of barium and salts, non-ferromagnetic metals, plastic, and detectable coatings.

6. The protective tissue cover of claim 1, wherein the third layer includes at least one material selected from the group consisting of a machine-scan detectable material, a controllable thermogenic material, and medicinal material.

7. The protective tissue cover of claim 1, wherein the first and second layers include perforations for tearing the protective tissue cover to a desired length.

8. The protective tissue cover according to claim 1, wherein the first layer includes a plurality of microtubes formed through, the microtubes permit passage of fluids between the first layer and the second layer.

9. The protective tissue cover of claim 8, further comprising a suction shroud covering at least a portion of the first layer, the suction shroud having an adapter for selective connection to a suction device.

\* \* \* \* \*